United States Patent [19]

Fukushima et al.

[11] Patent Number: 4,743,591
[45] Date of Patent: May 10, 1988

[54] COMPOSITION FOR ANIMALS

[75] Inventors: Mitsuru Fukushima; Yoshinori Hattori, both of Shizuoka; Takeo Shimura, Yono; Manabu Kozasa, Omiya, all of Japan

[73] Assignee: Toyo Jozo Company, Shizuoka, Japan

[21] Appl. No.: 946,664

[22] Filed: Dec. 24, 1986

Related U.S. Application Data

[63] Continuation of Ser. No. 672,418, Nov. 16, 1984, abandoned.

[30] Foreign Application Priority Data

Dec. 1, 1983 [JP] Japan ................. 58-228257

[51] Int. Cl.$^4$ ............. A61K 31/70; A61K 31/71
[52] U.S. Cl. ............................. 514/30; 514/34
[58] Field of Search ......................... 514/30, 34

[56] References Cited

U.S. PATENT DOCUMENTS 4,291,021 9/1981 Otani et al. ..................... 435/75
4,447,421 5/1984 Klothen ......................... 514/30

FOREIGN PATENT DOCUMENTS 0073390 3/1983 European Pat. Off. ............. 514/30

Primary Examiner—J. R. Brown
Assistant Examiner—Elli Peselel
Attorney, Agent, or Firm—Ladas & Parry

[57] ABSTRACT

Disclosed is a composition for treatment or prevention of diseases of animals or for addition to feeds for acceleration of growth which contains a mycinamicin antibiotic and at least one compound selected from the group consisting of a quinoxaline-di-N-oxide and a tetracycline antibiotic as effective ingredients. Administration of this composition affords excellent synergistic effects in antibacterial action and good body weight gaining effect and growth accelerating effect.

14 Claims, No Drawings

COMPOSITION FOR ANIMALS

This is a continuation of co-pending application Ser. No. 672,418 filed on Nov. 16, 1984, now abandoned.

This invention relates to a composition for treatment or prevention of diseases of animals or for additives to feeds of animals which contains a mycinamicin antibiotic and at least one substance selected from the group consisting of a quinoxaline-di-N-oxide compound and a tetracycline antibiotic as effective ingredients.

The quinoxaline-di-N-oxide compounds (called "QNO compounds" hereinafter) include, for example, compounds represented by the following formula [I]:

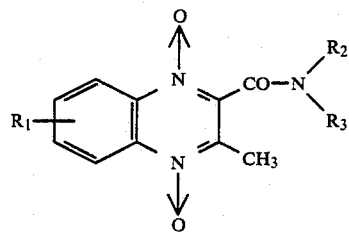

[I]

wherein $R_1$ represents hydrogen atom, chlorine atom, a lower alkyl group of 1 to 4 carbon atoms or an alkoxy group of 1 to 4 carbon atoms, $R_2$ and $R_3$ each represent hydrogen atom, hydroxyl group or alkyl groups of 1 to 4 carbon atoms which may be substituted with alkoxy, carboalkoxy, monoalkylamino or dialkylamino group or $R_3$ represents cyclohexyl group or $R_2$ and $R_3$ together with the nitrogen atom to which $R_2$ and $R_3$ bond may form a 5-membered or 6-membered heteroring. Alternatively, the 5-membered or 6-membered heteroring is substituted with alkyl group of 1 to 4 carbon atoms, said alkyl group being further substituted or not with hydroxy, methoxy or acetoxy group.

As examples of these compounds, mention may be made of olaquindox [N-(2-hydroxyethyl)-3-methyl-2-quinoxaline-carboxamido-1,4-di-N-oxide] (called "OQD" hereinafter) and those of $R_1$=hydrogen atom, $R_2$=propyl group and $R_3$=hydrogen atom (melting point: 172° C.); $R_1$=hydrogen atom, $R_2$=isopropyl group and $R_3$=hydrogen atom (melting point: 208° C. decomp.); $R_1$=hydrogen atom, $R_2$=butyl group and $R_3$=hydrogen atom (melting point: 136° C.); $R_1$=hydrogen atom, $R_2$=methoxyethyl group and $R_3$=hydrogen atom (melting point: 135° C.); $R_1$=hydrogen atom, $R_2$=methoxypropyl group and $R_3$=hydrogen atom (melting point: 141° C.); $R_1$=hydrogen atom, $R_2$=piperazinoethyl group and $R_3$=hydrogen atom (melting point: 218° C. decomp.); $R_1$=hydrogen atom, $R_2$=methyl group and $R_3$=methyl group (melting point: 189° C.); $R_1$=hydrogen atom, $R_2$=ethyl group and $R_3$=ethyl group (melting point: 162° C.); $R_1$=6-chloro group, $R_2$=methoxyethyl group and $R_3$=hydrogen atom (melting point: 183° C.); $R_1$=6-methyl group, $R_2$=methoxyethyl group and $R_3$=hydrogen atom (melting point: 169° C.); $R_1$=6-methoxy group, $R_2$=methoxyethyl group and $R_3$=hydrogen atom (melting point: 190° C.); $R_1$=methyl group, $R_2$=methyl group and $R_3$=hydrogen atom (melting point: 202° C.); $R_1$=hydrogen atom, $R_2$=dimethyl aminopropyl group and $R_3$=hydrogen atom (melting point: 154° C.), etc. There may be further mentioned carbadox [methyl-3-(2-quinoxalinylmethylene)carbazate-N-dioxide] (called "CBD" hereinafter), cyadox[2-formylquinoxaline 1,4-dioxide.cyanoacetylhydrazone], etc.

The tetracycline antibiotics (called "TC antibiotics" hereinafter) include antibiotics represented by the following formula [II]:

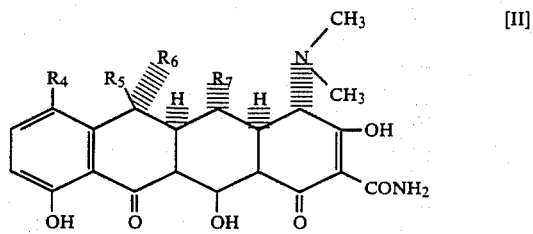

[II]

wherein $R_4$ represents hydrogen atom, chlorine atom or dimethylamino group, $R_5$ represents hydrogen atom or hydroxyl group, $R_6$ represents hydrogen atom or methyl group, $R_5$ and $R_6$ together may form methylene group and $R_7$ represents hydrogen atom or hydroxyl group. As examples thereof, mention may be made of tetracycline ($R_4$=hydrogen atom, $R_5$=hydroxyl group, $R_6$=methyl group and $R_7$=hydrogen atom), chlorotetracycline ($R_4$=chlorine atom, $R_5$=hydroxyl group, $R_6$=methyl group and $R_7$=hydrogen atom: called "CTC" hereinafter), oxytetracycline ($R_4$=hydrogen atom, $R_5$=hydroxyl group, $R_6$=methyl group and $R_7$=hydroxyl group: called "OTC" hereinafter), dimethylchlorotetracycline ($R_4$=chlorine atom, $R_5$=hydroxyl group, $R_6$=hydrogen atom, and $R_7$=hydrogen atom), metacycline ($R_4$=hydrogen atom, $R_5$ and $R_6$ together form a methylene group and $R_7$=hydroxyl group), doxycycline ($R_4$=hydrogen atom, $R_5$=hydrogen atom, $R_6$=methyl group and $R_7$=hydroxyl group: called "DOXY" hereinafter), minocycline ($R_4$=dimethylamino group, $R_5$=hydrogen atom, $R_6$=hydrogen atom and $R_7$=hydrogen atom), etc.

As examples of nontoxic salts of these QNO compounds and TC antibiotics, mention may be made of hydrochlorides, sulfates, phosphates, carbonates, ammonium salts, sodium salts, calcium salts, aluminum salts, alkyltrimethylammonium calcium salts, etc.

These QNO compounds and TC antibiotics have been widely used for treatment or prevention of disease of animals or as additives to feeds for animals.

The inventors have unexpectedly found that use of at least one of these QNO compounds and TC antibiotics in combination with a mycinamicin antibiotic exhibits excellent synergistic effect in antibacterial property and furthermore affords good body weight gaining effect and growth accelerating effect which shows improved feeding efficiency when they are added to feeds for animals and thus these compounds and antibiotics can be used as compositions for application to animals.

This invention has been accomplished based on the above findings and provides a composition for treatment or prevention of diseases of animals or as additives to feeds for animals which contains at least one member selected from the group consisting of QNO compounds and TC antibiotics and a mycinamicin antibiotic as effective ingredients.

QNO compounds and TC antibiotics which are effective ingredients in the compositions of this invention include those compounds as exemplified above. Especially preferred are OQD and CBD as QNO compounds and CTC, OTC, DOXY and their nontoxic salts as TC antibiotics.

The mycinamicin antibiotics include antibiotic mycinamicin represented by the following formula [III]:

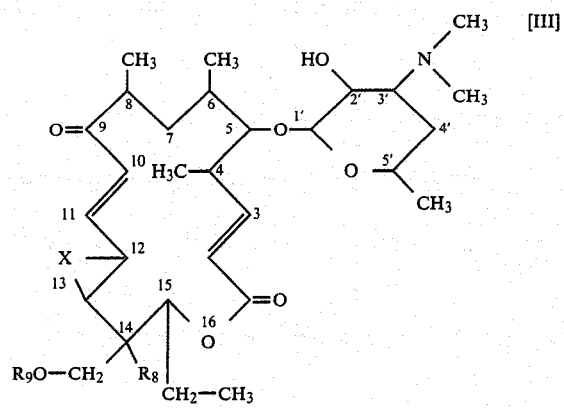

wherein X represents epoxy group or a direct linkage, $R_8$ represents hydrogen atom or hydroxyl group and $R_9$ represents hydrogen atom, or hexose ring represented by the following formula [IV]:

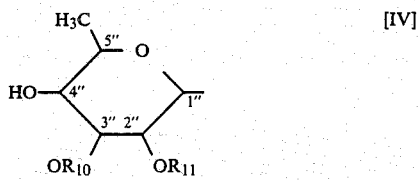

wherein $R_{10}$ represents hydrogen atom or a lower alkyl group and $R_{11}$ represents hydrogen atom or a lower alkyl group. These mycinamicin antibiotics may be used in a free form or in a form of their derivatives or salts.

As the mycinamicin antibiotics, there may be illustrated, among others, mycinamicin I (called "MI" hereinafter), mycinamicin II (MII), mycinamicin III (MIII), mycinamicin IV (MIV), mycinamicin V (MV), mycinamicin VI (MVI) and mycinamicin IX (MIX). MI is an antibiotic represented by the formula (III) [hereinafter referred to as antibiotic (III)] wherein X=epoxy, $R_8$=hydrogen, $R_9$=hexose ring, $R_{10}$=methyl and $R_{11}$=methyl. MII is an antibiotic (III) wherein X=epoxy, $R_8$=hydroxy, $R_9$=hexose ring, $R_{10}$=methyl and $R_{11}$=methyl. MIII is an antibiotic (III) wherein X=direct linkage, $R_8$=hydrogen, $R_9$=hexose ring, $R_{10}$=hydrogen and $R_{11}$=methyl. MIV is an antibiotic (III) wherein X=direct linkage, $R_8$=hydrogen, $R_9$=hexose ring, $R_{10}$=methyl and $R_{11}$=methyl. MV is an antibiotic (III) wherein X=direct linkage, $R_8$=hydroxy, $R_9$=hexose ring, $R_{10}$=methyl and $R_{11}$=methyl. MVI is an antibiotic (III) wherein X=direct linkage, $R_8$=hydrogen, $R_9$=hexose ring, $R_{10}$=hydrogen and $R_{11}$=hydrogen. MIX is an antibiotic (III) wherein X=direct linkage, $R_8$=hydrogen and $R_9$=hydrogen (demycinosyl-MIV).

These antibiotic compounds can be obtained by culturing Micromonospora sp. A 11725 strain (FERM-P No. 4488=NRRL 11452) belonging to genus Micromonospora in a medium, taking the product out of the cultured medium and, if necessary, converting X=epoxy group between 12 and 13 positions to direct linkage. (See U.S. Pat. No. 4,291,021; J.C.S. Chem. Comm., 1980, 120; Japanese Published Unexamined Patent Application Nos. 148,701/1979, 115,900/1980, and 122,799/1980; the specifications of Japanese Patent Application Nos. 194,141/1981 and 36,602/1982.) It may be added that U.S. Pat. No. 4,291,021 illustrates in its description the minute characteristics of the Micromonospora sp. A 11725 strain referred to above, and that the antibiotics A 11725 I, A 11725 II, A 11725 III, A 11725 Ia, and A 11725 IIa in the description correspond, respectively, the MI, MII, MIII, MIV and MV antibiotics.

As the derivatives of the mycinamicin antibiotics, there may be exemplified an antibiotic (III) wherein hydroxyl group at 4″-position of the mycinosyl ring is esterified or etherified.

Another exemplary preparation method of the mycinamicin antibiotics is the cultivation of Micromonospora polytrota NRRL 12066 (ATCC 31,584) in a medium, followed by taking the cultured product out of the medium. (Japanese Published Unexamined Patent Application No. 83,3497/1981.)

The salts of the mycinamicin antibiotics employed herein may be nontoxic inorganic and organic acid salts. There may be illustrated phosphate and hydrochloride salts as the inorganic acid salts. Organic acid salts are hydroxy-carboxylate such as tartrate, lactate, malate, citrate and gluconate; polycarboxylate such as malonate, succinate, maleate, fumarate and glutarate; and amino acid salts such as aspartate and glutaminate.

As the mycinamicin antibiotics, one of them or a mixture of two or more may be used in the purified or crude state.

The mycinamicin antibiotics are weakly basic antibiotics and soluble in an acidic water, methanol, acetone but insoluble in a basic water. To prepare the salts of the mycinamicin antibiotics, acccordingly, an mycinamicin in an inert solvent may be added to an aqueous solution of an acidic substance chosen, such as inorganic acid, hydroxycarboxylic acid, polycarboxylic acid and amino acid, and the objective salt formed is taken after the drying. These acidic salts have been illustrated above. Further, the QNO compounds, TC antibiotics and the mycinamicin antibiotics may be used as they are or, alternatively, they may be used by granulating or processing with binders, perfume, surface active agents, integrators, dispersing adjuvants, stabilizers, preservatives or excipients, as required.

The proportion of at least one compound selected from the group consisting of QNO compounds and TC antibiotics to the mycinamicin antibiotic is 1/10-10/1, preferably ¼-4/1.

The compositions for treatment and prevention of diseases of animals or for additives to feeds for growth acceleration of animals may be prepared in the form of parenteral injections, ointments, infusions, drinking preparations, marine animal preparations from these effective ingredients at said proportions.

These compositions for treatment or prevention of diseases of animals may be prepared by utilizing various known pharmaceutical recipes. For example, the injections may be prepared as aqueous or oily injections and the former is especially preferred.

The injections may contain at least one compound selected from the group consisting of QNO compounds and TC antibiotics in an amount of 1 to 20 mg and the mycinamicin antibiotic in an amount of 0.5 to 10 mg per 1 kg of body weight of animals per one day. The injections containing the effective ingredients at such ratio may be incorporated with preservatives, solubilization agents, surfactants, etc.

The ointments and infusions are preferably dermatologic ointments and udder and uterine infusions. These may be prepared using oily bases such as liquid paraffins, purified lanolin, vaselin, edible oils, e.g., safflower oil and rape seed oil and waxes or aqueous bases such as propylene glycol, glycerine, ethylene glycol, polyethylene glycol, etc. with addition of the effective ingredients and if necessary, surfactants, preservatives, dispersing agents, etc.

These ointments and infusions may contain 1 to 2000 mg of at least one compound selected from the group consisting of QNO compounds and TC antibiotics and 1 to 2000 mg of the mycinamicin antibiotic for one dosage.

These injections, ointments and infusions may ordinarily be administered once a day, but may also be administered twice or more a day.

In case of drinking preparations, they may contain 10 to 2000 mg of at least one compound selected from the group consisting of QNO compounds and TC antiobiotics and 5 to 1000 mg of the muycinamicin antibiotic per 1 kg of a drinking liquid, e.g., drinking water or emulsion. These QNO compounds or TC antibiotics and the mycinamicin antibiotic may be merely mixed with each other or if necessary, surfactants, dissolution assistants, coloring agents, etc. may be used for preparation.

In case of preparations for marine animals, these may contain at least one compound selected from the group consisting of QNO compounds and TC antibiotics in an amount of 1 to 200 mg and the mycinamicin antibiotic in an amount of 1 to 100 mg per 1 kg of body weight of animals per one day. The preparations may be prepared by merely mixing these effective ingredients at said ratio or may be prepared in the form of powder or granule with optionally using diluting agents such as lactose, sucrose or dextrin, dispersing agents such as talc and binders such as carboxymethylcellulose or methylcellulose. Moreover, this preparations may be added to fish baits.

Those which are prepared as mentioned above are used for treatment or prevention of diseases of animals.

Furthermore, at least one compound selected from the group consisting of QNO compounds and TC antibiotics and the mycinamicin antibiotic are incorporated in a feed, i.e., final assorted feed, in an amount of 0.5 to 2000 mg and 0.5 to 500 mg, respectively per 1 kg of the feed to prepare a composition for growth acceleration of animals shown by improved body weight gaining effect and improved feeding efficiency.

These feeds may be those of livestock including edible and pet animals, for poultry and for marine animals.

Further, the feeds may be in various forms, for example, animal crude feeds produced by brending grains, hays, green gresses, soiling crops, silages, root crops, etc. which are rich in crude fiber components; enriched concentrated feeds rich in digestible nutrient which are produced by blending grains, rice brans, oil meals, etc. which are low in crude fiber content and small in volume with crude feeds such as straws; and premixes which are produced by blending the enriched concentrated feeds, vitamines, aminoacids, antibacterial agent, inorganic material with a suitable carrier such as powders of soybean cake, brans, defatted rice brans and crops; and final assorted feeds to be given to animals as they are. The QNO compounds or TC antibiotics and the mycinamicin antibiotic may be added to the feeds in any forms mentioned above so that they may be contained at the ratios as mentioned above in the final assorted feeds.

These effective ingredients may be added to feeds by any conventional methods. For example, they may be added previously to feed materials or they may be added at the time of mixing of feed materials or before administration of feeds by means of mixing, immersing, spraying, etc., if necessary using a mixer and then they may be homogeneously mixed.

The feed materials include, for example, grains such as corn, rice, wheat, milo, rice bran, wheat bran, etc.; straws, grasses or brans rich in crude fibrous material; oil cakes from cotton seed, soy bean and safflower; meats; powdered bones; fish meals and soybean powder; fatty oils, such as cotton seed oil, peanut oil, corn oil, sesame oil, etc.; yeasts, alphalpha, lactose, sucrose, glucose, methionine and choline chloride; vitamins, such as vitamin A, vitamin D, vitamin E, vitamin $K_1$, vitamin $K_2$, vitamin $B_1$, vitamin $B_2$, vitamin $B_6$, vitamin $B_{12}$, calcium pantothenate, folic acid, etc.; talc, Japanese acid clay, calcium carbonate, magnesium sulfate, potassium iodide, calcium phosphate, sodium chloride, etc. They may be used in alone or as a mixture. These materials may additionally contain, as case may require, another antibiotic substance, such as colistin and penicillin- and amino acid-group antibiotics, sulfa drugs; hemostatic agent, such as tranexamic acid; anthelmintics, enzymatic agents, lactobacillus preparations, anticeptics, tasting agents, emulsifying agents, wetting agents and solubilizing agents. They may be selected and prepared according to the recipe shown in "Feed and Feeding" (Morrison Publishing Company, Clinton, Iowa, 1959), for each type of breeding and the kind of animals, aimed by the professionals. For instance, the feeds containing 50 to 80% of grains with the supplemental vitamins, 5 to 35% of animal and vegetable proteins and 2 to 5% of minerals are suitable for animals like swine.

Furthermore, to these feeds may also be added the QNO compounds or TC antibiotics and the mycinamicin antibiotic for treatment or prevention of diseases of animals. In this case, 0.5 to 2000 mg of at least one compound selected from the group consisting of QNO compounds and TC antibiotics and 0.5 to 500 mg of the mycinamicin antibiotic may be added per 1 kg of feed.

The animals to which the present compositions are applied include livestock and poultry and marine animals which may be edible or pet animals. As livestock, mention may be made of swine, cow, horse, sheep, goat, rabbit, dog, cat, rat, mouse, mink, etc. As poultry, mention may be made of egg-laying or edible fowls, duck, goose, turkey, quail, pheasant, macaw, pigeon, etc. As marine animals, mention may be made of sea animals such as young yellowtail, sea bream, shrimp, etc. and fresh-water animals such as trout, carp, eel, ayu-fish, etc.

Thus prepared compositions in small dosages have treating and protecting effects against various infections such as respiratory diseases and gastrointestinal diseases of livestock, respiratory diseases of poultry and specific diseases of marine animals which are caused by bacteria, for example, *Mycoplasma gallisepticum, Mycoplasma synoviae* (Mycoplasma infection: fowls), *Mycoplasma hyorhinis, Mycoplasma hyopneumoniae, Mycoplasma hyosynoviae* (Mycoplasma infections: swine), *Mycoplasma bovirhinis, Mycoplasma bovigenitalium, Myco-*

*plasma bovis* (Mycoplasma infections: cows), *Ureaplasma* (pneumonitis: cows), *Mycoplasma meleagridis* (Mycoplasma infections: turkeys), *Haemophilus paragallinarum* (infections coryza: fowls), *Haemophilus pleuropneumoniae* (Haemophilus infections: swine), *Toreponeama hyodysenteriae* (swine dysentery: swine), *Corynebacterium pyogenes* (Cornybacterium infections: cows, swine), *Fusobacterium necrophorum* (hepatoabscess: cows), *Clostridium perfringens* (Clostridium infections: fowls, swine), *Pasturella multocida* (Pasturella infections: cows, swine), *Escherichia coli* (Escherichia infections: cows, turkeys, cows, swine), bacteria such as *Salmonella enteritidis* and *Salmonella typhimurium* which belong to Salmonella genus (Salmonella infections: fowls, cows, swine), bacteria belonging to Staphylococcus genus (e.g., *Staphylococcus aureus*: Staphylococcus infections: fowls, cows, swine), bacteria belonging to Storeptococcus genus (e.g., *Streptococcus agalactiae, Streptococcus equisimilis*: Streptococcus infections: fowls, cows, swine, yellowtails), bacteria belonging to Aeromonas genus (e.g., *Aeromonas hydrophila*: red pest, scale protrusion disease: eels, carps), bacteria belonging to Edwardsiella genus (e.g., *Edwardsiella tarda*: Edwardsiellosis: eels), etc.

Furthermore, feeds to which the present compositions are added increase the growing rate, improve the feeding efficiency and show exceeding body weight gaining effect, that it, growth accelerating effect.

The effects obtained according to this invention and compositions of this invention will be exemplified in the following Examples, but they are not construed to limit this invention.

EXAMPLE 1

Synergistic effects of the QNO compounds or TC antibiotics and the mycinamicin antibiotic on various strains were measured by BOX method with liquid medium [disclosed in Susumu Mihashi's "Method for measurement of Sensitivity of Chemicals" pages 84–86, 1980].

The tested strains were as follows:

*Escherichia coli* B, *Escherichia coli* NIHJJC-2, *Salmonella typhosa* H901, *Salmonella enteritidis* Gaertner, *Staphylococcus aureus* ATCC 6538P, *Streptococcus pyogenes* N.Y.5, *Streptococcus faecalis* 1501. OQD and CBD as QNO compounds, OTC hydrochloride (called merely "OTC" in this Example) as TC antibiotics and MI.phosphate (called merely "MI" in this Example) as the mycinamicin antibiotics were used and amounts of these compounds are shown by mcg/ml.

The results are shown below, from which synergistic effects on the strains will be recognized.

(1) Results on *Escherichia coli* B are shown in Table 1 (MI and OTC) and Table 2 (MI and CBD).

TABLE 1

| Amount of MI | Amount of OTC | Amount of MI | Amount of OTC |
|---|---|---|---|
| 50 | 0 | 3.13 | 0.39 |
| 25 | 0.025 | 1.56 | 1.56 |
| 12.5 | 0.05 | 0 | 3.13 |
| 6.25 | 0.2 | | |

TABLE 2

| Amount of MI | Amount of CBD | Amount of MI | Amount of OTC |
|---|---|---|---|
| 50 | 0 | 6.25 | 3.13 |
| 25 | 0.20 | 0 | 6.25 |

TABLE 2-continued

| Amount of MI | Amount of CBD | Amount of MI | Amount of OTC |
|---|---|---|---|
| 12.5 | 0.20 | | |

(2) Results on *Escherichia coli* NIHJ JC-2 are shown in Table 3 (MI and OTC), Table 4 (MI and OGD) and Table 5 (MI and CBD).

TABLE 3

| Amount of MI | Amount of OTC | Amount of MI | Amount of OTC |
|---|---|---|---|
| 100 | 0 | 12.5 | 0.39 |
| 50 | 0.10 | 6.25 | 0.78 |
| 25 | 0.10 | 0 | 1.56 |

TABLE 4

| Amount of MI | Amount of OQD | Amount of MI | Amount of OQD |
|---|---|---|---|
| 100 | 0 | 12.5 | 12.5 |
| 50 | 0.78 | 6.25 | 50 |
| 25 | 6.25 | 0 | 100 |

TABLE 5

| Amount of MI | Amount of CBD | Amount of MI | Amount of CBD |
|---|---|---|---|
| 100 | 0 | 12.5 | 0.20 |
| 50 | 0.05 | 0 | 0.39 |
| 25 | 0.10 | | |

(3) Results on *Salmonella typhosa* H901 are shown in Table 6 (MI and OTC) and Table 7 (MI and CBD).

TABLE 6

| Amount of MI | Amount of OTC | Amount of MI | Amount of OTC |
|---|---|---|---|
| 100 | 0 | 6.25 | 0.78 |
| 50 | 0.10 | 3.13 | 1.56 |
| 25 | 0.20 | 0 | 3.13 |
| 12.5 | 0.39 | | |

TABLE 7

| Amount of MI | Amount of CBD | Amount of MI | Amount of CBD |
|---|---|---|---|
| 100 | 0 | 6.25 | 3.13 |
| 50 | 0.78 | 3.13 | 3.13 |
| 25 | 0.78 | 0 | 6.25 |
| 12.5 | 1.56 | | |

(4) Results on *Salmonella enteritidis* Gaertner are shown in Table 8 (MI and OTC), Table 9 (MI and OQD) and Table 10 (MI and CBD).

TABLE 8

| Amount of MI | Amount of OTC | Amount of MI | Amount of OTC |
|---|---|---|---|
| 200 | 0 | 12.5 | 0.79 |
| 100 | 0.025 | 6.25 | 1.56 |
| 50 | 0.10 | 0 | 3.13 |
| 25 | 0.39 | | |

TABLE 9

| Amount of MI | Amount of OQD | Amount of MI | Amount of OQD |
|---|---|---|---|
| 200 | 0 | 25 | 12.5 |
| 100 | 6.25 | 12.5 | 25 |

TABLE 9-continued

| Amount of MI | Amount of OQD | Amount of MI | Amount of OQD |
|---|---|---|---|
| 50 | 12.5 | 0 | 50 |

TABLE 10

| Amount of MI | Amount of CBD | Amount of MI | Amount of CBD |
|---|---|---|---|
| 200 | 0 | 12.5 | 3.13 |
| 100 | 0.20 | 6.25 | 6.25 |
| 50 | 0.39 | 3.13 | 12.5 |
| 25 | 1.56 | 0 | 25 |

(5) Results on *Staphylococcus aureau* ATCC 6538P are shown in Table 11 (MI and OTC) and Table 12 (MI and CBD).

TABLE 11

| Amount of MI | Amount of OTC | Amount of MI | Amount of OTC |
|---|---|---|---|
| 0.05 | 0 | 0.0063 | 0.10 |
| 0.025 | 0.025 | 0 | 0.20 |
| 0.0125 | 0.05 | | |

TABLE 12

| Amount of MI | Amount of CBD | Amount of MI | Amount of CBD |
|---|---|---|---|
| 0.05 | 0 | 0.0125 | 6.25 |
| 0.025 | 0.39 | 0 | 12.5 |

(6) Results on *Streptococcus pyogenes* N.Y. 5 are shown in Table 13 (MI and OTC) and Table 14 (MI and (CBD).

TABLE 13

| Amount of MI | Amount of OTC | Amount of MI | Amount of OTC |
|---|---|---|---|
| 0.05 | 0 | 0.0063 | 0.10 |
| 0.025 | 0.025 | 0.0032 | 0.20 |
| 0.0125 | 0.05 | 0 | 0.39 |

TABLE 14

| Amount of MI | Amount of CBD | Amount of MI | Amount of CBD |
|---|---|---|---|
| 0.05 | 0 | 0.0063 | 6.25 |
| 0.025 | 3.13 | 0 | 12.5 |
| 0.0125 | 3.13 | | |

(7) Results on *Streptococcus faecalis* 1501 are shown in Table 15 (MI and OQD) and Table 16 (MI and CBD).

TABLE 15

| Amount of MI | Amount of OQD | Amount of MI | Amount of OQD |
|---|---|---|---|
| 12.5 | 0 | 0.78 | 200 |
| 6.25 | 25 | 0.39 | >400 |
| 3.13 | 50 | 0 | >400 |
| 1.56 | 50 | | |

TABLE 16

| Amount of MI | Amount of CBD | Amount of MI | Amount of CBD |
|---|---|---|---|
| 12.5 | 0 | 1.56 | 12.5 |
| 6.25 | 1.56 | 0.78 | >50 |

TABLE 16-continued

| Amount of MI | Amount of CBD | Amount of MI | Amount of CBD |
|---|---|---|---|
| 3.13 | 6.25 | 0 | >50 |

EXAMPLE 2

Using five young swine, the body weight gaining effects and feed efficiencies were examined by breeding them for 5 weeks with giving feeds prepared by adding MI.phosphate and OQD to swine starter feed for latter period having the constituents as shown in Table 17 and fully homogeneously mixing them by a twin-cylinder mixer (test groups were classified as shown in Table 18).

TABLE 17

| Constituents | Content |
|---|---|
| Crude protein | 19.0% |
| Crude fat | 5.0% |
| Crude fibrous material | 1.8% |
| Crude ash | 5.7% |
| Ca | 1.08% |
| P | 0.95% |
| DCP | 17.4% |
| TDN | 82.1% |
| GE | 361 Cal./100 g |

DCP: Digestible crude protein
TDN: Total digestible nutrient
GE: Gross energy

TABLE 18

| Test group | Concentration of MI | Concentration of OQD |
|---|---|---|
| group 1 | 5 ppm | 5 ppm |
| group 2 | 5 ppm | 10 ppm |
| group 3 | 5 ppm | 20 ppm |
| group 4 | 10 ppm | 20 ppm |
| group 5 | 10 ppm | 40 ppm |
| group 6 | 2.5 ppm | 10 ppm |
| group 7 | 2.5 ppm | 20 ppm |
| group 8 | no addition | no addition |

The average body weight, body weight gain and weight gain index (average per a body in each group) of the swine during the test period are shown in Table 19 and feed intake and feed efficiency (average per one body in each group) are shown in Table 20.

The results show that joint use of at least 2.5 ppm of MI and at least 10 ppm of OQD provides the effects intended by this invention, and joint use of 5 to 10 ppm of MI and 10 to 40 ppm of OQD provides good effects and is preferred.

TABLE 19

| Group | At the start (kg) | At the end (kg) | Body weight gain (kg) | Weight gain index (%) |
|---|---|---|---|---|
| 1 | 6.4 ± 1.00 | 16.2 ± 1.91 | 9.7 ± 0.92 | 108 |
| 2 | 6.5 ± 0.92 | 17.1 ± 1.93 | 10.6 ± 1.07 | 118 |
| 3 | 6.5 ± 0.80 | 17.7 ± 2.05 | 11.1 ± 1.30* | 123 |
| 4 | 6.5 ± 0.78 | 17.4 ± 1.74 | 10.9 ± 1.06* | 121 |
| 5 | 6.4 ± 0.14 | 17.6 ± 1.76 | 11.2 ± 1.05* | 124 |
| 6 | 6.4 ± 0.89 | 16.3 ± 1.99 | 10.0 ± 1.12 | 111 |
| 7 | 6.4 ± 0.61 | 16.3 ± 1.54 | 9.9 ± 0.97 | 110 |
| 8 | 6.4 ± 0.64 | 15.4 + 1.38 | 9.0 ± 0.81 | 100 |

*Significant difference with 5% ratio of risk (Same is applied hereinafter)

TABLE 20

| Group | Feed intake (kg) | Feed efficiency |
|---|---|---|
| 1 | 17.8 | 1.83 |
| 2 | 20.5 | 1.93 |

TABLE 20-continued

| Group | Feed intake (kg) | Feed efficiency |
|---|---|---|
| 3 | 19.3 | 1.74 |
| 4 | 19.5 | 1.79 |
| 5 | 19.3 | 1.72 |
| 6 | 18.4 | 1.84 |
| 7 | 18.5 | 1.87 |
| 8 | 18.0 | 2.00 |

EXAMPLE 3

Example 2 indicates that joint use of mycinamicin antibiotic and OQD at a small ratio of 5 ppm:20 ppm (Group 3 in Example 2) afforded superior effects. Thus, body weight gaining effect and feed efficiency were obtained in the same manner as in Example 2 except that the additives as shown in classification of test groups of Table 21 were used in place of MI.phosphate and OQD used in Example 2.

TABLE 21

| Test group | Additives (Concentration) |
|---|---|
| group 1 | No addition |
| group 2 | MI · phosphate [10 ppm] |
| group 3 | MII · phosphate [10 ppm] |
| group 4 | Mmix · phosphate [10 ppm] |
| group 5 | OQD [40 ppm] |
| group 6 | MI · phosphate + OQD [5 ppm + 20 ppm] |
| group 7 | MII · phosphate + OQD [5 ppm + 20 ppm] |
| group 8 | Mmix · phosphate + OQD [5 ppm + 20 ppm] |

In Table 21, Mmix contains 25% of MI, 70% of MII and 5% of others such as MIII, IV, V, VI, IX, etc.

Average body weight, body weight gain and weight gain index per a body during the course of the test are shown in Table 22 and feed intake and feed efficiency are shown in Table 23. The results show that joint use of MI, MII or Mmix and OQD gave superior effects to those of any single uses.

TABLE 22

| Group | At the start (kg) | At the end (kg) | Body weight gain (kg) | Weight gain index (%) |
|---|---|---|---|---|
| 1 | 6.9 ± 0.86 | 15.7 ± 1.64 | 8.8 ± 0.83 | 100 |
| 2 | 6.8 ± 0.78 | 16.9 ± 2.14 | 10.1 ± 1.46 | 115 |
| 3 | 6.9 ± 0.64 | 16.3 ± 1.82 | 9.5 ± 1.32 | 108 |
| 4 | 6.9 ± 0.68 | 16.5 ± 1.46 | 9.6 ± 0.99 | 109 |
| 5 | 6.9 ± 0.83 | 16.3 ± 1.79 | 9.5 ± 1.02 | 108 |
| 6 | 6.8 ± 0.76 | 17.7 ± 2.07 | 11.0 ± 1.26* | 125 |
| 7 | 6.9 ± 0.95 | 17.5 ± 1.99 | 10.6 ± 1.08* | 120 |
| 8 | 6.8 ± 1.05 | 17.6 ± 2.29 | 10.8 ± 1.29* | 123 |

TABLE 23

| Group | Feed intake (kg) | Feed efficiency | Group | Feed intake (kg) | Feed efficiency |
|---|---|---|---|---|---|
| 1 | 17.8 | 2.02 | 5 | 17.9 | 1.88 |
| 2 | 18.3 | 1.81 | 6 | 19.4 | 1.76 |
| 3 | 18.2 | 1.92 | 7 | 20.1 | 1.90 |
| 4 | 17.8 | 1.85 | 8 | 19.5 | 1.81 |

EXAMPLE 4

Five young swine were bred 5 weeks by giving feeds prepared by fully homogeneously mixing MIV.phosphate and OTC.alkyltrimethylammonium calcium salt (called "OTC.quaternary ammonium" hereinafter) with the feed as shown in Table 17 of Example 2 (test groups are classified as shown in Table 24). Body weight gaining effect and feed efficiency were obtained.

TABLE 24

| | Concentration of MIV | Concentration of OTC. quaternary ammonium |
|---|---|---|
| group 1 | 5 ppm | 5 ppm |
| group 2 | 5 ppm | 10 ppm |
| group 3 | 5 ppm | 20 ppm |
| group 4 | 10 ppm | 20 ppm |
| group 5 | 10 ppm | 40 ppm |
| group 6 | 2.5 ppm | 10 ppm |
| group 7 | 2.5 ppm | 20 ppm |
| group 8 | no addition | no addition |

Average body weight, weight gain and weight gain index per a body during the course of the test are shown in Table 25 and feed intake and feed efficiency are shown in Table 26. The results show that the effects of this invention can be obtained by joint use at least 5 ppm of MIV and at least 10 ppm of OTC.quaternary ammonium and especially good effects are obtained by the joint use of 5 to 10 ppm MIV and 20 to 40 ppm of OTC-.quaternary ammonium.

TABLE 25

| Group | At the start (kg) | At the end (kg) | Body weight gain (kg) | Weight gain index (%) |
|---|---|---|---|---|
| 1 | 7.0 ± 0.72 | 16.8 ± 2.01 | 9.7 ± 1.29 | 104 |
| 2 | 7.0 ± 0.82 | 17.4 ± 2.03 | 10.4 ± 1.25 | 112 |
| 3 | 7.1 ± 0.74 | 18.4 ± 1.88 | 11.3 ± 1.16* | 122 |
| 4 | 7.0 ± 0.61 | 18.2 ± 1.60 | 11.2 ± 1.01* | 120 |
| 5 | 7.1 ± 0.66 | 18.5 ± 1.87 | 11.4 ± 1.21* | 123 |
| 6 | 7.0 ± 0.88 | 16.9 ± 1.81 | 9.9 ± 0.95 | 106 |
| 7 | 7.0 ± 0.71 | 17.1 ± 2.10 | 10.1 ± 1.41 | 109 |
| 8 | 7.0 ± 0.64 | 16.3 ± 1.59 | 9.3 ± 0.98 | 100 |

TABLE 26

| Group | Feed intake (kg) | Feed efficiency | Group | Feed intake (kg) | Feed efficiency |
|---|---|---|---|---|---|
| 1 | 19.2 | 1.98 | 5 | 20.0 | 1.75 |
| 2 | 18.7 | 1.80 | 6 | 18.8 | 1.90 |
| 3 | 19.7 | 1.74 | 7 | 18.6 | 1.84 |
| 4 | 19.9 | 1.78 | 8 | 19.1 | 2.05 |

EXAMPLE 5

Weight gaining effect and feed efficiency were obtained in the same manner as in Example 2 except that additives are shown in classification of test groups of Table 27 were used in placed of MI.phosphate and OQD used in Example 2.

TABLE 27

| Test group | Additives (Concentration) |
|---|---|
| group 1 | No addition |
| group 2 | Mmix · phosphate [10 ppm] |
| group 3 | CBD [40 ppm] |
| group 4 | OTC · hydrochloride [40 ppm] |
| group 5 | OTC · quaternary ammonium [40 ppm] |
| group 6 | Mmix · phosphate + CBD [5 ppm + 20 ppm] |
| group 7 | Mmix · phosphate + OTC · hydrochloride [5 ppm + 20 ppm] |
| group 8 | Mmix · phosphate + OTC · quaternary ammonium [5 ppm + 20 ppm] |

Average body weight, body weight gain and weight gain index per a body during the course of the test are shown in Table 28 and feed intake and feed efficiency are shown in Table 29. The results indicate that joint use of Mmix and CBD, OTC.hydrochloride or OTC.quaternary ammonium gave superior effects to those of any single uses.

TABLE 28

| Group | At the start (kg) | At the end (kg) | Body weight gain (kg) | Weight gain index (%) |
|---|---|---|---|---|
| 1 | 7.8 ± 1.01 | 16.7 ± 1.63 | 8.9 ± 0.64 | 100 |
| 2 | 7.8 ± 0.68 | 17.7 ± 1.78 | 9.9 ± 1.12 | 111 |
| 3 | 7.7 ± 0.94 | 17.1 ± 2.11 | 9.4 ± 1.21 | 106 |
| 4 | 7.7 ± 1.05 | 17.4 ± 2.38 | 9.7 ± 1.34 | 109 |
| 5 | 7.8 ± 1.03 | 17.4 ± 2.42 | 9.6 ± 1.43 | 108 |
| 6 | 7.7 ± 1.02 | 18.7 ± 2.26 | 11.0 ± 1.25* | 124 |
| 7 | 7.6 ± 1.08 | 18.4 ± 2.12 | 10.8 ± 1.05* | 121 |
| 8 | 7.7 ± 1.08 | 18.9 ± 2.42 | 11.2 ± 1.38 | 126 |

TABLE 29

| Group | Feed intake (kg) | Feed efficiency | Group | Feed intake (kg) | Feed efficiency |
|---|---|---|---|---|---|
| 1 | 18.0 | 2.02 | 5 | 17.5 | 1.82 |
| 2 | 18.2 | 1.84 | 6 | 20.7 | 1.88 |
| 3 | 18.4 | 1.94 | 7 | 19.0 | 1.76 |
| 4 | 17.8 | 1.83 | 8 | 20.0 | 1.79 |

EXAMPLE 6

Weight gaining effect and feed efficiency were obtained in the same manner as in Example 2 except that the additives are shown in the classification of test groups of Table 30 were used in plase of MI.phosphate and OQD used in Example 2.

TABLE 30

| Test group | Additives (Concentration) |
|---|---|
| group 1 | No addition |
| group 2 | M IV · phosphate [10 ppm] |
| group 3 | CTC [40 ppm] |
| group 4 | DOXY · hydrochloride [40 ppm] |
| group 5 | M IV · phosphate + CTC [5 ppm + 20 ppm] |
| group 6 | M IV · phosphate + DOXY · hydrochloride [5 ppm + 20 ppm] |

Average body weight, weight gain and weight gain index per a body during the course of the test are shown in Table 31 and feed intake and feed efficiency are shown in Table 32. These results indicate that the joint use of MIV and CTC or DOXY.hydrochloride provided superior effects to those of any single uses.

TABLE 31

| Group | At the start (kg) | At the end (kg) | Body weight gain (kg) | Weight gain index (%) |
|---|---|---|---|---|
| 1 | 6.6 ± 0.99 | 15.1 ± 1.31 | 8.6 ± 0.64 | 100 |
| 2 | 6.5 ± 0.67 | 16.1 ± 1.16 | 9.5 ± 0.62 | 110 |
| 3 | 6.6 ± 0.98 | 15.7 ± 1.34 | 9.2 ± 0.76 | 107 |
| 4 | 6.6 ± 0.87 | 15.9 ± 1.39 | 9.4 ± 0.78 | 109 |
| 5 | 6.5 ± 0.97 | 16.8 ± 1.58 | 10.3 ± 0.82* | 120 |
| 6 | 6.6 ± 0.81 | 16.8 ± 1.50 | 10.2 ± 0.86* | 119 |

TABLE 32

| Group | Feed intake (kg) | Feed efficiency | Group | Feed intake (kg) | Feed efficiency |
|---|---|---|---|---|---|
| 1 | 19.6 | 1.96 | 4 | 19.6 | 1.80 |
| 2 | 21.1 | 1.90 | 5 | 18.0 | 1.76 |
| 3 | 19.0 | 1.78 | 6 | 20.8 | 1.73 |

EXAMPLE 7

Body weight gaining effect and feed efficiency were obtained on twenty domestic fowls (broilers) which were bred for 3 weeks with feeds prepared by sufficiently homogeneously mixing in a mixer the additives as shown in the test groups of Table 3 with chicken starter feed for having the constituents as shown in Table 34.

TABLE 33

| Group | Additives (Concentration) |
|---|---|
| group 1 | No addition |
| group 2 | M I · phosphate [5 ppm] |
| group 3 | M II · phosphate [5 ppm] |
| group 4 | M mix · phosphate [5 ppm] |
| group 5 | OTC · phosphate [20 ppm] |
| group 6 | OTC · quaternary ammonium [20 ppm] |
| group 7 | DOXY · hydrochloride [20 ppm] |
| group 8 | M I · phosphate + OTC · quaternary ammonium [2.5 ppm + 10 ppm] |
| group 9 | M II · phosphate + OTC · quaternary ammonium [2.5 ppm + 10 ppm] |
| group 10 | M mix · phosphate + OTC · quaternary ammonium [2.5 ppm + 10 ppm] |
| group 11 | M mix · phosphate + OTC · hydrochloride [2.5 ppm + 10 ppm] |
| group 12 | M mix · phosphate + DOXY · hydrochloride [2.5 ppm + 10 ppm] |

TABLE 34

| Constituents | | Constituents | |
|---|---|---|---|
| Crude protein | 20.0% | Ca | 1.03% |
| Crude fat | 3.4% | P | 0.83% |
| Crude fibrous material | 3.4% | GE | 3.49 Cal/100 g |
| Crude ash | 5.5% | ME | 292 Cal/100 g |

ME: Metabolic Energy

Average body weight, body weight gain and weight gain index per a body during the course of the test are shown in Table 35 and feed intake and feed efficiency are shown in Table 36. The results show that the joint use of MI, MII or Mmix and OTC or DOXY afforded superior effects to those of any single uses.

TABLE 35

| Group | At the start (g) | At the end (g) | Body weight gain (g) | Weight gain index (%) |
|---|---|---|---|---|
| 1 | 43.7 ± 2.52 | 612.3 ± 54.39 | 568.7 ± 52.18 | 100 |
| 2 | 43.0 ± 2.74 | 649.1 ± 52.89 | 606.1 ± 50.67* | 107 |
| 3 | 43.5 ± 2.47 | 636.7 ± 52.43 | 592.7 ± 54.64 | 104 |
| 4 | 43.0 ± 2.86 | 641.6 ± 56.22 | 598.6 ± 53.67 | 105 |
| 5 | 43.5 ± 2.54 | 643.3 ± 47.74 | 599.8 ± 45.55 | 105 |
| 6 | 44.0 ± 2.59 | 645.2 ± 52.14 | 601.1 ± 49.87* | 106 |
| 7 | 43.4 ± 3.04 | 622.4 ± 57.79 | 579.0 ± 44.95 | 102 |
| 8 | 44.4 ± 2.68 | 695.0 ± 55.82 | 650.6 ± 53.32** | 114 |
| 9 | 43.3 ± 3.11 | 672.5 ± 44.10 | 629.2 ± 41.11** | 111 |
| 10 | 43.4 ± 2.98 | 691.5 ± 57.06 | 648.1 ± 54.30** | 114 |
| 11 | 44.0 ± 2.89 | 681.1 ± 57.18 | 637.6 ± 55.32** | 112 |
| 12 | 43.1 ± 2.97 | 659.7 ± 57.36 | 616.6 ± 54.63* | 108 |

**Significant difference with 1% ratio of risk

TABLE 36

| Group | Feed intake (g) | Feed efficiency | Group | Feed intake (g) | Feed efficiency |
|---|---|---|---|---|---|
| 1 | 847.4 | 1.49 | 7 | 868.5 | 1.50 |
| 2 | 891.0 | 1.47 | 8 | 917.3 | 1.41 |
| 3 | 877.2 | 1.48 | 9 | 880.9 | 1.40 |
| 4 | 874.0 | 1.46 | 10 | 900.9 | 1.39 |
| 5 | 881.7 | 1.47 | 11 | 899.0 | 1.41 |
| 6 | 877.6 | 1.46 | 12 | 875.6 | 1.42 |

EXAMPLE 8

Body weight gaining effects were examined on five Holstein-Friesians (male) of one week old which were bred for 4 weeks with feeds prepared by mixing the additives as shown in each test group of Table 37 with artificial milk A [crude protein 28.0% or more, digestible crude protein 25.5%, total digestible nutrient at least 98%].

TABLE 37

| Group | Additives (Concentration) |
|---|---|
| group 1 | No addition |
| group 2 | M mix · phosphate [10 ppm] |
| group 3 | OTC · hydrochloride [40 ppm] |
| group 4 | M mix · phosphate + OTC · hydrochloride [5 ppm + 20 ppm] |

Average body weight, body weight gain and weight gain index of Holstein-Friesians per a body during the course of the test are shown in Table 38. Results show that joint use of mycinamicin and OTC afforded superior effects to those of single use.

TABLE 38

| Group | At the start (kg) | At the end (kg) | Body weight gain (kg) | Weight gain index (%) |
|---|---|---|---|---|
| 1 | 41.7 ± 5.23 | 61.8 ± 6.84 | 20.0 ± 1.67 | 100 |
| 2 | 41.2 ± 5.16 | 62.7 ± 7.38 | 21.5 ± 2.24 | 108 |
| 3 | 40.9 ± 3.89 | 62.0 ± 6.08 | 21.1 ± 2.22 | 106 |
| 4 | 41.3 ± 5.51 | 64.5 ± 7.45 | 23.2 ± 1.95* | 116 |

EXAMPLE 9

Death rates were obtained on about 1000 of infant young yellowtales in each group to which were given for 21 days the feed prepared by fully homogeneously mixing additives as shown in each test group of Table 39 with sardines and mackerels.

TABLE 39

| Test Group | Additives [Concentration] |
|---|---|
| group 1 | No addition |
| group 2 | M mix · phosphate [25 ppm] |
| group 3 | DOXY · hydrochloride [100 ppm] |
| group 4 | M mix · phosphate + DOXY · hydrochloride [12.5 ppm + 50 ppm] |

Note: Feeds were given in October

As shown in Table 40, joint use of mycinamicin antibiotic and DOXY gave superior effects.

TABLE 40

| Group | Number of fishes at the start | Number of dead fishes | Number of living fishes | Dead rate |
|---|---|---|---|---|
| group 1 | 1020 | 135 | 885 | 13.2% |
| group 2 | 1006 | 88 | 918 | 8.7 |
| group 3 | 1018 | 93 | 925 | 9.1 |
| group 4 | 1025 | 41 | 984 | 4.0 |

[Note]
Main causes for death were found to be storeptococcal diseases by isolation of bacteria and dissection.

EXAMPLE 10

Treatment test for respiratory mycoplasma disease (CRD) of domestic fowls

120 Domestic fowls having CRD were tested on effect of joint use of Mmix.phosphate and OTC.hydrochloride according to the test prescription as shown in Table 41. The joint use effect was clearly recognized as shown in Table 42.

TABLE 41

| Group | Compounds used | Dosage | Period and method of administration | Number of tested fowls |
|---|---|---|---|---|
| 1 | Mmix · phosphate | 0.005% | Continuous administration for 3 days | 30 |
|  | OTC · hydrochloride | 0.025% | Administration by adding to drinking water |  |
| 2 | Mmix · phosphate | 0.01% | Administration by adding to drinking water | 30 |
| 3 | OTC · hydrochloride | 0.05% | Administration by adding to drinking water | 30 |
| 4 | None | — | — | 30 |

TABLE 42

| Group | Clinical symptom Positive rate | Score for air sac lesion (average value) | Isolation of bacteria Positive rate |
|---|---|---|---|
| Before administration ||||
| 1 | 100 | 1.7 | 80(%) |
| 2 | 100 | 1.5 | 90 |
| 3 | 100 | 1.5 | 80 |
| 4 | 100 | 1.4 | 70 |
| Administration of one week ||||
| 1 | 0 | 0.1 | 0 |
| 2 | 0 | 0.2 | 10 |
| 3 | 45 | 0.6 | 30 |
| 4 | 75 | 1.1 | 80 |
| Administration of 3 weeks ||||
| 1 | 0 | 0.0 | 0 |
| 2 | 0 | 0.0 | 0 |
| 3 | 20 | 0.4 | 10 |
| 4 | 40 | 0.9 | 30 |

[Note]
Clinical symptoms: Swollen face, nasal mucus, dyspnea.
Score for air sac lesion:
1 ... Muddiness,
2 ... Sticking of cheese-like material,
3 ... Heavy sticking of cheese-like material,
4 ... Peritonitis

EXAMPLE 11

Treatment test for diarrhea of young swine

Effect of joint use of MIV.phosphate and OQD and OTC was tested on 50 swine having diarrhea caused by colitis germs according to the test prescriptions as shown in Table 43. The joint use effects of mycinamicin with other chemicals were clearly recognized as shown in Table 44.

TABLE 43

| Group | Compounds used | Dosage | Period and method of administration | Number of tested fowls |
|---|---|---|---|---|
| 1 | MIV · phosphate | 25 ppm | Administered for 5 days by adding to feeds | 10 |
|  | OQD | 25 ppm |  |  |
| 2 | MIV · phosphate | 25 ppm | Administered for 5 days by adding to feeds | 10 |
|  | OTC | 100 ppm |  |  |
| 3 | OQD | 50 ppm | Administered for 5 days by adding to feeds | 10 |
| 4 | OTC | 200 ppm | Administered for 5 days by adding to feeds | 10 |

TABLE 43-continued

| Group | Compounds used | Dosage | Period and method of administration | Number of tested fowls |
|---|---|---|---|---|
| 5 | None (Control) | — | — | 10 |

Test 44
Test results

| | State of feces | | | |
|---|---|---|---|---|
| Group | +++ Watery diarrhea | ++ Mushy diarrhea | + Loose feces | − Normal feces |
| Before administration | | | | |
| 1 | 40% | 60% | 0% | 0% |
| 2 | 30 | 70 | 0 | 0 |
| 3 | 20 | 70 | 10 | 0 |
| 4 | 10 | 60 | 30 | 0 |
| 5 | 20 | 40 | 20 | 0 |
| Administration of one day | | | | |
| 1 | 0 | 10 | 70 | 20 |
| 2 | 0 | 10 | 90 | 0 |
| 3 | 10 | 50 | 40 | 0 |
| 4 | 10 | 40 | 50 | 0 |
| 5 | 30 | 30 | 40 | 0 |
| Administration of 3 days | | | | |
| 1 | 0 | 0 | 0 | 100 |
| 2 | 0 | 0 | 0 | 100 |
| 3 | 0 | 20 | 60 | 20 |
| 4 | 0 | 30 | 70 | 0 |
| 5 | 20 | 70 | 10 | 0 |
| Administration of 5 days | | | | |
| 1 | 0 | 0 | 0 | 100 |
| 2 | 0 | 0 | 0 | 100 |
| 3 | 0 | 0 | 30 | 70 |
| 4 | 0 | 0 | 10 | 90 |
| 5 | 30 | 60 | 10 | 0 |

EXAMPLE 12

Treatment test for pneumonia of cows

Effect of joint use of Mmix.phosphate and OTC.hydrochloride was tested on 20 young cows having pneumonia according to the test prescriptions as shown in Table 45. As a result, the joint use effect of mycinamicin with other chemicals was clearly recognized as shown in Table 46.

TABLE 45

| | Test Groups | | | |
|---|---|---|---|---|
| Group | Compounds used | Dosage | Period and method of administration | Number of tested fowls |
| 1 | Mmix · phosphate | 1 mg(p)/kg | One a day for 1–3 days by intravenous injection | 5 |
| | OTC · hydrochloride | 5 mg(p)/kg | | |
| 2 | Mmix · phosphate | 2 mg(p)/kg | One a day for 1–3 days by intravenous injection | 5 |
| 3 | OTC · hydrochloride | 10 mg(p)/kg | One a day for 1–3 days by intravenous injection | 5 |
| 4 | None (Control) | — | One a day for 1–3 days by intravenous injection | 5 | p: potency

TABLE 46

Test results

| | | Clinical symptoms | | | |
|---|---|---|---|---|---|
| | | Before admini- | Administration | | |
| Group | Number of cows | stration | One day | 2 days | 3 days |
| 1 | 5 | 100% | 20% | 0% | 0% |
| 2 | 5 | 100 | 40 | 20 | 0 |
| 3 | 5 | 100 | 60 | 40 | 40 |
| 4 | 5 | 100 | 100 | 100 | 80 |

[Notes]
Clinical symptoms: fever, cough, dyspnea, nasal mucus.

EXAMPLE 13

50 g of OTC and 50 g of Mmix.phosphate were mixed with de-fatted bran by a twin-cylinder mixer to make up 1 kg to obtain a composition for addition to a feed. This composition is administered by incorporating in an amount of 0.04 to 0.4% in an assorted feed for swine, cows or domestic fowls.

EXAMPLE 14

50 g CTC and 50 g of MI.phosphate were homogeneously mixed with corn powders to make up 1 kg to obtain a composition for addition to feeds. This composition is administered by incorporating in an amount of 0.04 to 0.4% in an assorted feed for swine, cows or domestic fowls.

EXAMPLE 15

10 g of OQD and 50 g of Mmix.phosphate were homogeneously mixed with de-fatted bran to make up 1 kg to obtain a composition for addition to feeds. This composition is administered by incorporating in an amount of 0.04 to 0.4% in an assorted feed for swine, cows or domestic fowl.

EXAMPLE 16

5 g of CBD and 25 g of MII.phosphate were homogeneously mixed with soybean cake to obtain 500 g of a composition to be added to feeds. This composition is administered by incorporating in an amount of 0.04 to 0.4% in an assorted feed for swine, cows and domestic fowls.

EXAMPLE 17

12.5 g of DOXY.hydrochloride and 25 g of Mmix.phosphate were mixed with lactose to make up 500 g. This composition may be administered as drinking preparations by dissolving in an amount of 0.4 to 4 g in 1 l of drinking water in case of domestic fowls, in an amount of 0.04 to 0.4 g per 1 kg of body weight per a day in drinking water or milk in case of cows and in an amount of 0.02 to 0.2 g per 1 kg of body weight per a day in drinking water in case of swine. In case of giving to fishes, the composition may be used as preparations obtained by incorporating it in an amount of 0.05 to 1.5 g per 1 kg of body weight per a day in a raw food (sardine, etc.) or an assorted feed.

EXAMPLE 18

25 g of OTC.hydrochloride and 25 g of MI.phosphate were homogeneously mixed with dextrin to make 500 g. This composition may be used in the same manner as in Example 14.

EXAMPLE 19

In a mixed liquid of 25 ml of propylene glycol and 25 ml of water was dissolved 0.5 g of magnesium chloride. In this solution were dissolved 5 g of OTC.hydrochloride and 2.5 g of MI.phosphate. Then, several drops of triethanolamine were added thereto to adjust the pH to 6.5-7.5 and thereafter propylene glycol was added to make up 100 ml. This composition is used as an intramuscular or intravenous injection in an amount of 0.02 to 0.2 ml per 1 kg of body weight per a day for swine and cows, 0.05 to 0.5 ml for domestic fowls and 0.02 to 0.4 ml for dogs and cats.

EXAMPLE 20

30 g of CTC and 30 g of Mmix.phosphate were added to 400 g of white vaseline, 300 g of liquid paraffin and 240 g of Plastibase (liquid paraffin containing 5% of a polyethylene resin manufactured by Squibb Japan Inc.) and these were kneaded to obtain a homogeneous composition. This composition is used in an amount of 0.5 to 10 g per one udder of cows as infusions for udders.

EXAMPLE 21

50 g of Macrogal 4000 and 50 g of Macrogal 400 were mixed, warmed to 65° C. with water bath to melt them and then cooled. Thereto were added 5 g of MI.phosphate and 5 g of OTC.hydrochloride and these were kneaded to prepare a homogeneous composition. This is used in an amount of 0.4 g to 10 g per one udder of cows as infusions for udders.

EXAMPLE 22

10 g OQD and 50 g of MIV were homogeneously mixed with a soybean cake to make up 500 g. This composition is used by incorporating in an amount of 0.04 to 0.4% in an assorted feed for swine, cows or domestic fowls.

EXAMPLE 23

50 g of OTC and 50 g of MIV were homogeneously mixed with a corn powder to make 1 kg of a composition. This is used by incorporating in an amount of 0.04 to 0.4% in an assorted feed for swine, cows or domestic fowls.

EXAMPLE 24

12.5 g of OTC.hydrochloride and 25 g of MIV.tartrate were mixed with lactose to make 500 g of a composition. This may be used as drinking preparations made by dissolving in an amount of 0.4 to 4 g in 1 l of a drinking water for domestic fowls, in an amount of 0.04 to 0.4 g per 1 kg of body weight per a day in a drinking water or milk for cows and in an amount of 0.02 to 0.2 g per 1 kg of body weight per a day in a drinking water for swine. For marine animals, this may be administered by incorporating it in an amount of 0.05 to 1.5 g per 1 kg of body weight per a day in a raw feed or an assorted feed.

What is claimed is:

1. A composition which comprises compound (A) selected from the group consisting of (I) and (II), said (I) being quinoxaline-di-N-oxide compounds having the formula (I):

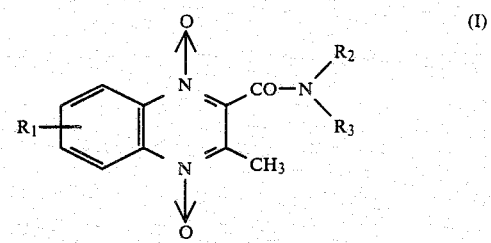

wherein $R_1$ represents hydrogen atom, chlorine atom, a lower alkyl group of 1 to 4 carbon atoms or an alokoxy group of 1 to 4 carbon atoms, $R_2$ and $R_3$ each represent hydrogen atoms, hydroxyl groups or alkyl groups of 1 to 4 carbon atoms which may be substituted with alkoxy, carboalkoxy, monoalkylamino or dialkylamino group or $R_3$ represents cyclohexyl group or $R_2$ and $R_3$ together with the nitrogen atom to which $R_2$ and $R_3$ bond may form a 5-membered or 6-membered heteroring, said 5-membered or 6-membered heteroring may be substituted with alkyl group of 1 to 4 carbon atoms, said alkyl group being further substituted or not with hydroxy, methoxy or acetoxy group; and said (II) being tetracycline antibiotics having the formula (II) and non-toxic salts thereof:

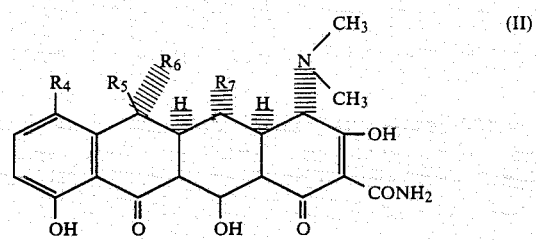

wherein $R_4$ represents hydrogen atom, chlorine atom or dimethylamino group, $R_5$ represents hydrogen atom or hydroxyl group, $R_6$ represents hydrogen atom or methyl group, $R_5$ and $R_6$ together may form methylene group and $R_7$ represents hydrogen atom or hydroxyl group; and mycinamicin antibiotics (B) having the formula (III) and non-toxic salts thereof:

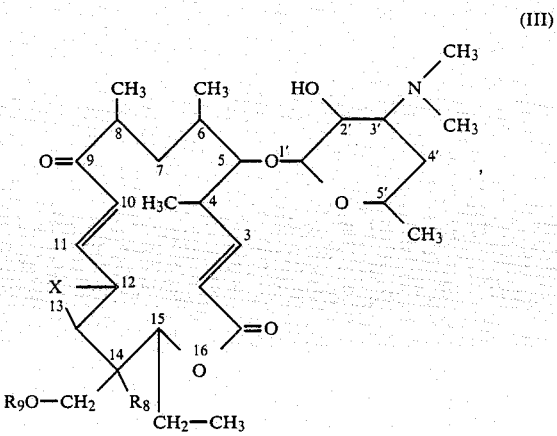

wherein X represents epoxy group or a direct linkage, R$_8$ represents hydrogen atom or hydroxyl group and R$_9$ represents hydrogen atom, or hexose ring represented by the following formula [IV]:

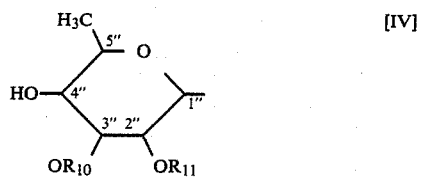

wherein R$_1$0 represents hydrogen atom or a lower alkyl group and R$_1$1 represents hydrogen atom or a lower alkyl group;

the ratio A/B being in the range of 1:10 to 10:1.

2. A composition according to claim 1 wherein the quinoxaline-di-N-oxide compound is olaquindox or carbadox.

3. A composition according to claim 1 wherein the tetracycline antibiotic is chlorotetracycline, oxytetracycline, doxycycline or notoxic salts thereof.

4. A composition according to claim 1 wherein the mycinamicin antibiotic is antibiotic mycinamicin in a free form or in a form of a derivative or a salt.

5. A composition according to claim 4 wherein the antibiotic mycinamicin is antibiotic mycinamicin I, II, III, IV, V, VI or IX.

6. A composition according to claim 4 wherein the salt is a phosphate, hydrochloride, tartrate, lactate, malate, citrate, gluconate, malonate, succinate, maleate, fumarate, glutarate, adipate, aspartate or glutaminate.

7. A composition according to claim 1 wherein the proportion is ¼ to 4/1.

8. A composition according to claim 1 wherein the composition is in the form of injections, ointments, infusions, drinking prepations or marine preparations.

9. A composition according to claim 8 wherein the injections comprise 1 to 20 mg of quinoxaline-di-N-oxide compound and the tetracycline antibiotic and 0.5 to 10 mg of the mycinamicin antibiotic per 1 kg of body weight of animals per day.

10. A composition according to claim 8 wherein the ointments and infusions comprise 1 to 2000 mg of the quinoxaline-di-N-oxide compound or the tetracycline antibiotic and 1 to 2000 mg of the mycinamicin antibiotic, as one dosage for animals.

11. A composition according to claim 8 wherein the drinking preparations comprise 10 to 2000 mg of the quinoxaline-di-N-oxide compound or the tetracycline antibiotic and 5 to 1000 mg of the mycinamicin antibiotic per 1 l of a drinking liquid.

12. A composition according to claim 8 wherein the marine preparations contain 1 to 200 mg of the quinoxaline-di-N-oxide compound or the tetracycline antibiotic and 1 to 100 mg of the mycinamicin antibiotic per 1 kg of body weight of animals per one day.

13. A composition for additives to feeds according to claim 1 which comprises 0.5 to 2000 mg of the quinoxaline compound and the tetracycline derivative and 0.5 to 500 mg of the mycinamicin antibiotic per 1 kg of feed.

14. A composition, as in claim 1, wherein said mycinamycin of the Formula III is mycinamycin I or II.

* * * * *